United States Patent
Black

(10) Patent No.: US 10,842,501 B2
(45) Date of Patent: Nov. 24, 2020

(54) SYSTEM AND METHOD FOR RAPIDLY ACCESSING AN IMPROVED TOURNIQUET

(71) Applicant: Bryan Black, Arlington, TX (US)

(72) Inventor: Bryan Black, Arlington, TX (US)

(*) Notice: Subject to any disclaimer, the term of this patent is extended or adjusted under 35 U.S.C. 154(b) by 0 days.

(21) Appl. No.: 15/455,923

(22) Filed: Mar. 10, 2017

(65) Prior Publication Data

US 2018/0256172 A1    Sep. 13, 2018

(51) Int. Cl.
| | |
|---|---|
| *A61B 17/00* | (2006.01) |
| *A61B 17/132* | (2006.01) |
| *A45F 5/02* | (2006.01) |
| *A61B 50/00* | (2016.01) |
| *A61B 50/20* | (2016.01) |
| *A61B 50/30* | (2016.01) |

(52) U.S. Cl.
CPC .......... *A61B 17/1322* (2013.01); *A45F 5/021* (2013.01); *A61B 50/00* (2016.02); *A61B 50/20* (2016.02); *A45F 2200/0566* (2013.01); *A61B 17/1327* (2013.01); *A61B 2050/005* (2016.02); *A61B 2050/0051* (2016.02); *A61B 2050/0085* (2016.02); *A61B 2050/314* (2016.02)

(58) Field of Classification Search
CPC ............ A61B 17/1322; A61B 17/1327; A45F 5/021; B65B 7/02; B65B 63/04
USPC ....................................................... 224/663
See application file for complete search history.

(56) References Cited

U.S. PATENT DOCUMENTS

| | | | |
|---|---|---|---|
| 3,190,444 A | 6/1965 | Kelson | |
| 4,140,164 A * | 2/1979 | Staup | A45C 13/18 150/110 |
| 4,506,769 A | 3/1985 | Franco et al. | |
| 4,513,866 A * | 4/1985 | Thomas | A45C 9/00 190/110 |
| 4,598,802 A * | 7/1986 | Abenaim | A45C 7/0036 190/107 |
| 4,811,768 A * | 3/1989 | Williams | A45C 1/04 150/102 |
| 5,170,919 A * | 12/1992 | DeSantis | A45C 1/04 224/192 |
| 5,207,303 A | 5/1993 | Oswalt | |
| H1363 H * | 10/1994 | Leeker | 206/225 |
| 5,779,122 A * | 7/1998 | Martinelli | A45C 11/24 224/222 |
| 5,850,754 A * | 12/1998 | Dobbins | A44B 15/005 70/456 R |

(Continued)

FOREIGN PATENT DOCUMENTS

| | | |
|---|---|---|
| CN | 204744297 U | 11/2015 |
| CN | 205198147 U | 5/2016 |

OTHER PUBLICATIONS

International Preliminary Report on Patentability from PCT/US2019/021999 dated Jan. 11, 2019.

(Continued)

*Primary Examiner* — Peter N Helvey
(74) *Attorney, Agent, or Firm* — James E. Walton

(57) ABSTRACT

A system and method for rapidly accessing a tourniquet located in a pouch with a pull-away cover. The tourniquet holder allows users to safely store in a fabric pouch a prepared tourniquet that is quickly accessible and coupled to a removable cover of the pouch. Users are able to fold tourniquet in a manner that allow the tourniquet to be removed from the pouch and used nearly instantaneously.

20 Claims, 6 Drawing Sheets

Fig. 5

(56) References Cited

U.S. PATENT DOCUMENTS

| | | | | |
|---|---|---|---|---|
| 5,893,370 | A * | 4/1999 | Perez | A41D 13/0012 |
| | | | | 2/94 |
| 6,508,391 | B2 * | 1/2003 | Gilbert | A61M 5/002 |
| | | | | 224/664 |
| 6,612,432 | B2 * | 9/2003 | Motson | A45F 5/00 |
| | | | | 206/305 |
| 7,410,083 | B2 * | 8/2008 | Reid | A45C 11/18 |
| | | | | 224/661 |
| 9,333,128 | B2 * | 5/2016 | Catrone | A61B 17/132 |
| 10,595,878 | B2 * | 3/2020 | Theodorou | A61B 50/31 |
| 2006/0289590 | A1 * | 12/2006 | Held | A45F 3/04 |
| | | | | 224/637 |
| 2007/0000965 | A1 * | 1/2007 | Cannon, Jr. | F41C 33/0218 |
| | | | | 224/673 |
| 2012/0302980 | A1 * | 11/2012 | Pidgeon | A45C 11/00 |
| | | | | 604/319 |
| 2016/0029777 | A1 * | 2/2016 | Gadams | A45F 5/00 |
| | | | | 224/222 |
| 2016/0135575 | A1 | 5/2016 | Solomon et al. | |
| 2018/0120056 | A1 * | 5/2018 | Chambers | F41C 33/046 |

OTHER PUBLICATIONS

International Search Report and Written Opinion from counterpart International Application No. PCT/US2018/021999, dated May 25, 2018.

\* cited by examiner

SYSTEM AND METHOD FOR RAPIDLY ACCESSING AN IMPROVED TOURNIQUET

BACKGROUND

1. Field of the Invention

The present invention relates generally to pouch for storing an improved tourniquet, and more specifically to a system and method for rapidly accessing a tourniquet.

2. Description of Related Art

Tourniquets are utilized to stop the flow of bleeding from trauma victims. Tourniquets conventionally are retained in an elongated holder with one end open much like a flashlight. However, tourniquets are not constructed like a flashlight and therefor a need exists for a tourniquet holder configured for the unique aspects of tourniquets as compared to flashlights. Thus, there exists significant room for improvement in the art for overcoming these and other shortcomings of conventional systems and methods for rapidly storing and accessing a tourniquet.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
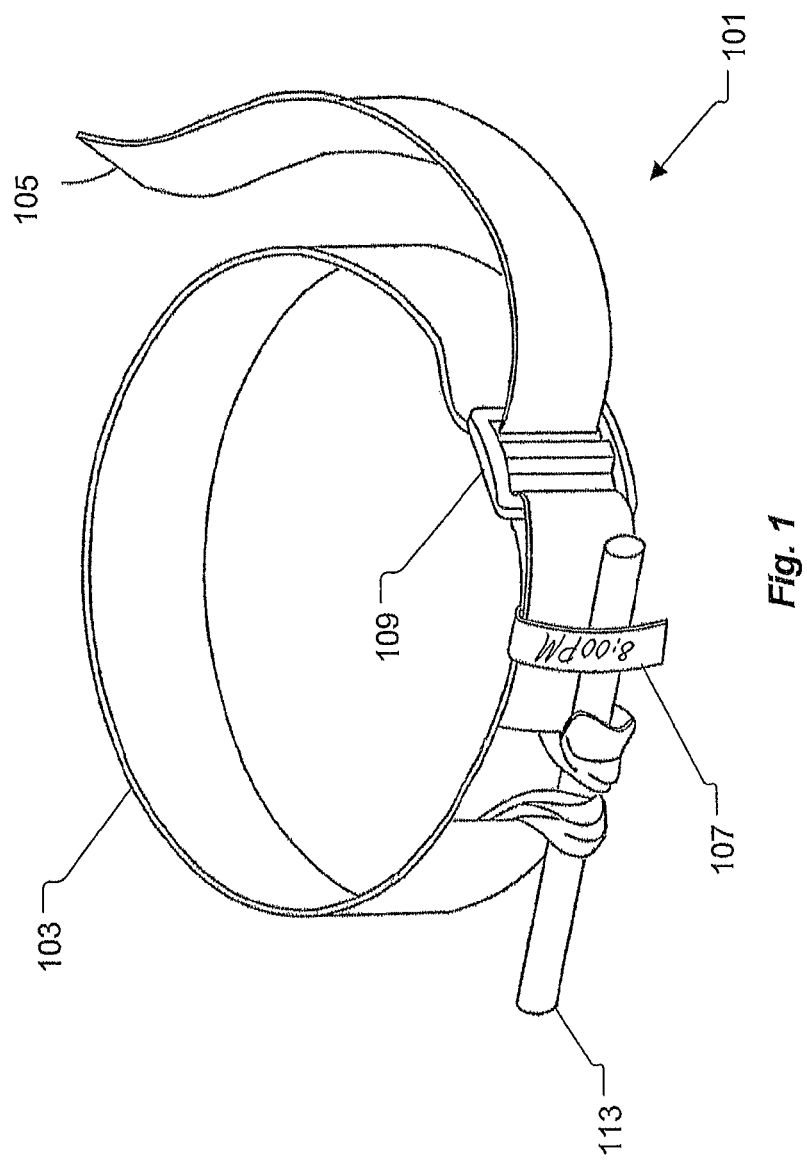
FIG. 1 is a perspective view of an improved tourniquet according to the present application.
Figure 2:
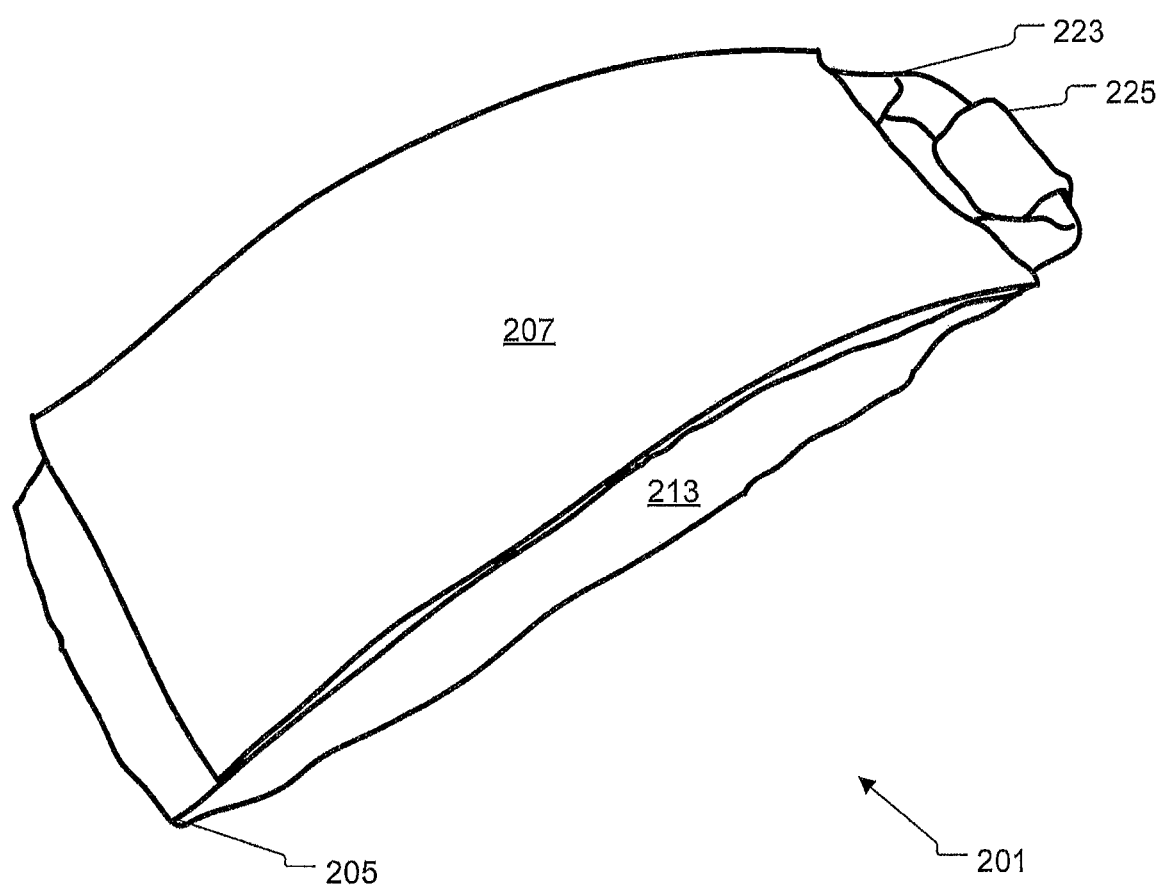
FIG. 2 is a perspective view of a tourniquet pouch according to the present application.
Figure 3:
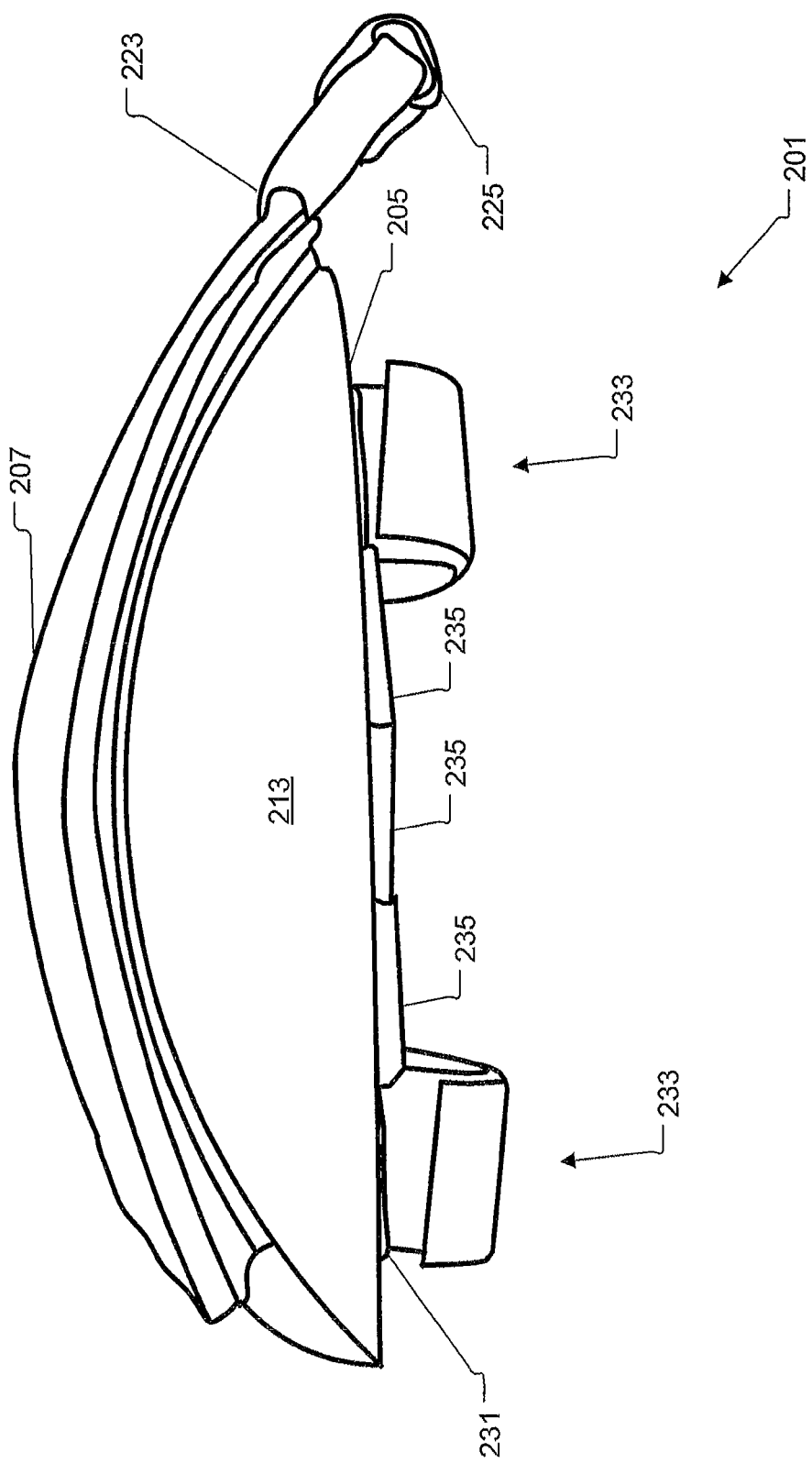
FIG. 3 is a generally side perspective view of a tourniquet pouch according to the present application.
Figure 4:
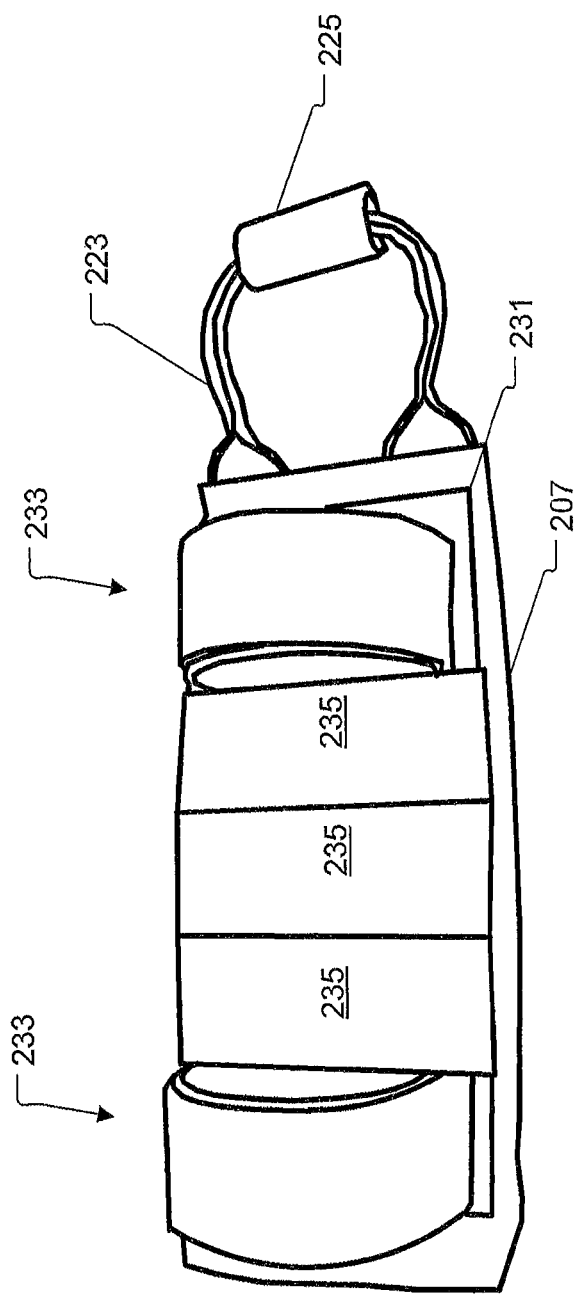
FIG. 4 is a generally upward perspective view of a tourniquet pouch according to the present application.
Figure 5:
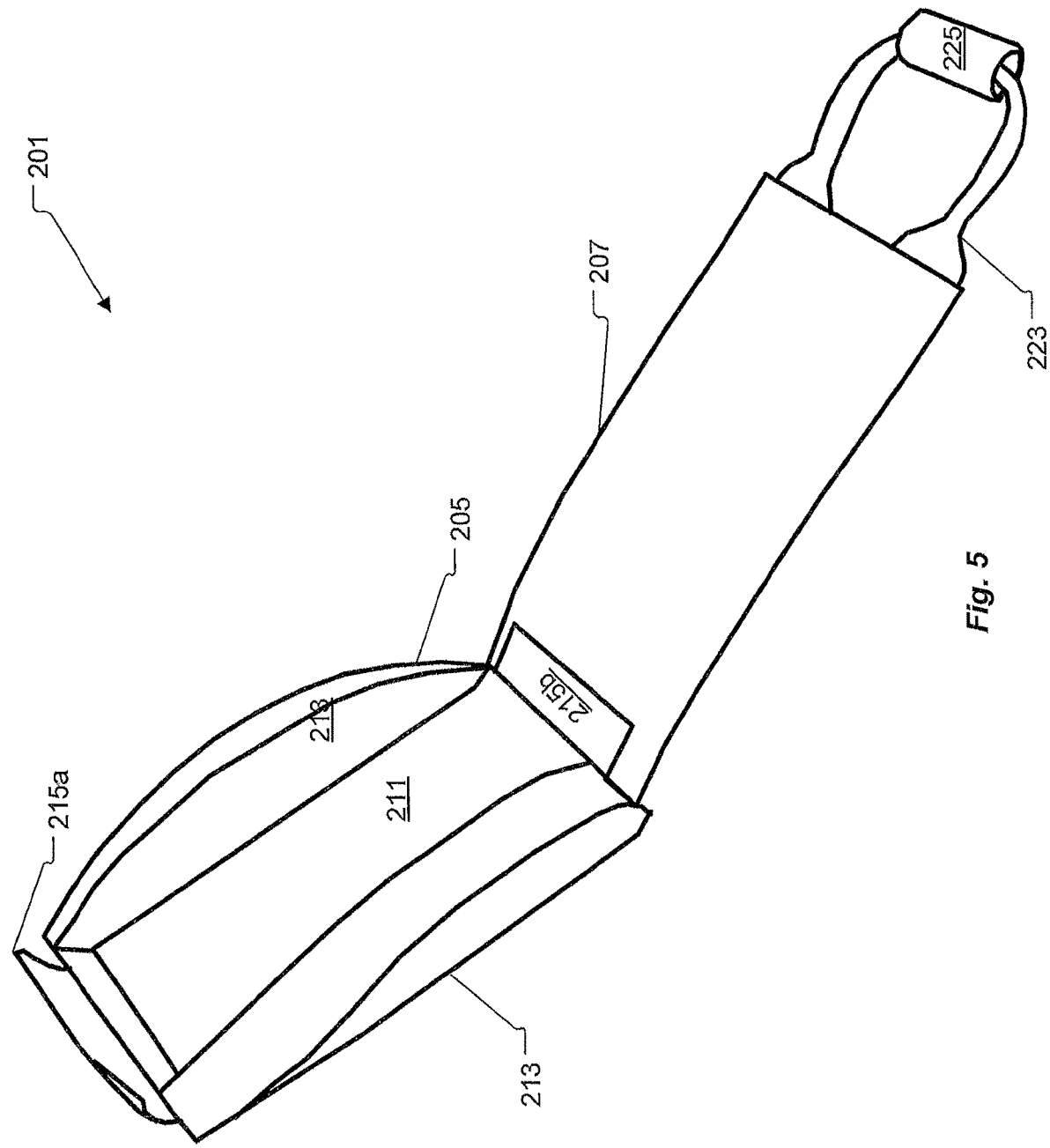
FIG. 5 is a perspective view of an open tourniquet pouch according to the present application.

While the assembly and method of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method for rapidly accessing a tourniquet are provided below. It will of course be appreciated that in the development of any actual embodiment, numerous implementation-specific decisions will be made to achieve the developer's specific goals, such as compliance with assembly-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Tourniquets save lives by reducing bleeding in emergencies. The amount of time to apply a tourniquet directly relates to the amount of blood loss and therefore the likelihood that the injured victim will survive the trauma. The quicker the tourniquet is applied, the less blood is loss, the more likely the injured will make it. Therefore, an improved tourniquet holder that reduces the amount of time to extract the tourniquet from the holder will reduce blood loss and reduce the loss of life.

Referring now also to FIG. 1 in the drawings, a preferred embodiment of an improved tourniquet according to the present application is illustrated. Tourniquet 101 is comprised of a strap 103 having an adjustable diameter with a tail 105, a time label 107, a buckle 109, and a windlass 113 for removal of slack in the tourniquet. Tourniquet 101 is primarily fabric and as such is highly flexible. The flexibility of the tourniquet is preferred as device is configured to squeeze the injured limb to stop the flow of blood.

Referring now to FIGS. 2-6B in the drawings, a preferred embodiment of improved tourniquet pouch according to the present application is illustrated. Pouch 201 is comprised of a mounted member 205 and a cover 207. Mounted member 205 is comprised of a lower member 211, a first and a second elongated side members 213, and a first tab 215a and second tab 215b. Cover 207 is comprised of an elongated member 221, a first handle 223, and a tag 225. Cover 207 further comprises tabs and slots, such as slot 227. Slot 227 connects first opening 229 to second opening 230. Slot 227 is configured to retain the tail of the tourniquet while stored inside of the pouch. While the preferred embodiment of the cover utilizes a first handle 223, it should be apparent that the cover alternatively further comprises a second handle opposite the first handle so the user can quickly remove the cover pulling either longitudinal direction relative to the pouch.

In the preferred embodiment, the first and second elongated members 213 as well as the first and second tabs 215 are covered in hook tape. Additionally, an inner surface of the cover 207 is covered in loop tape. Preferably the loop tape of the cover is retained by the hook tape of the mounted member. The hook and loop tape is configured to provide a removable and replaceable interface between the cover 207 and the mounted member 205. The first and second elongated members 213 as well as the first and second tabs 215 form a rectangular shaped opening for the tourniquet to be stored inside of and the rectangular shaped cover to close the rectangular shaped opening. In place of or in addition to the hook and loop tape a plurality of magnets and magnetic materials can be used to allow the cover to be quickly removed in an emergency.

In the preferred embodiment the tourniquet is folded and coupled to the removable cover while stored in the pouch. Upon use the cover is removed from the mounted member and the tourniquet is ready to be pulled away from the cover and utilized. Alternatively, the tourniquet is stored entirely inside the pouch and removed by the user after the cover has been removed.

The improved tourniquet pouch is designed as a way to mount, store, or quickly deploy a tourniquet. The included time label, with hook tape, can be affixed to the pouch cover interior as a supplement, but is not a replacement for the manufacturers instructed specifications. With the sewn in time label facing up, measure a 12 inch tail from the edge of the buckle to the end of the tail of the tourniquet. Flip the tourniquet over, so the 12 inch tail with the sewn in time label is facing down. Remove the tourniquet pouch cover from the body. Ensuring the side of the tourniquet tail with the sewn in time label is still facing down, pass the tail through the pouch cover opening closest to the pull handle. Continue passing the tail through the slot until it exits the bottom opening. Pull back the tail until the end is coupled near the bottom channel opening by coupling the hook side of the tail to the loop side of the cover. The user then grasps the tourniquet at its natural fold with the buckle facing them and checks that the tail still measures 12 inches and the buckle is securely fastened. Rotate the tourniquet to the backside so the windlass is now facing the user. Twist the windlass up and to the right to fold the nylon strap, aligning the windlass in a vertical orientation along the tourniquet body. Rotate the tourniquet back to the front side with the buckle facing towards the user. The user while holding the tourniquet body and windlass, grasps the remaining strap and the pouch cover in opposite hand. From the bottom, fold strap and the pouch cover up and behind the tourniquet body and windlass.

The user continues to fold the strap and the pouch cover over and on top of the tourniquet buckle. The pouch cover should now be facing the user with an outer surface of the pouch cover visible to the user. The user then tucks the loose strap loop upwards into the small void underneath the tourniquet buckle. Grasping the pouch, and ensuring the first tab is oriented towards the top. Orient the bottom channel opening of the pouch cover to the bottom of the pouch body and lift tourniquet tail to expose interior loop. Affix the prepared pouch cover to the second tab at the bottom of the pouch body. Fold pouch cover and tourniquet into pouch body. Adhere cover to pouch body side attachment tabs one at a time, ensuring top remains open. Before securing cover to the first tab, ensure tourniquet windlass is out of the way by pressing it down into the pouch. Secure cover to first tab. The pouch is now loaded and ready for deployment.

To deploy, pull outward on the handle away from the pouch body, exposing the tourniquet. The user then follows tourniquet manufacturer's instructions for application to the appendage.

Pouch 201 further comprised a mounting system 231. Mounting system 231 is comprised of an elongated member having an area smaller than the mounted member 205. Narrow ends of the mounting system 231 are attached to the mounted member 205 typically through sewing however other attachments are contemplated by this application such as fusing, bonding, and welding. Mounting system 231 further comprises a first and a second adjustable strap 233, and a plurality of fixed diameter straps 235. Mounting system 231 is configured to allow a user to mount the pouch at least four different ways. First, the user can attach the pouch 201 to a backpack by wrapping the first and second adjustable straps around the backpack's shoulder straps. Second, the user can mount the pouch horizontal on a belt by inserting the belt through the plurality of fixed diameter straps 235. Third, the user can mount the pouch 201 vertically on a belt by inserting the belt between the mounting system 231 and the mounted member 205. Fourth, the user can couple the pouch 201 to a MOLLE based attachment area with the use of Malice clips. Alternatively the pouch can be sewed directly to the surface of the user's clothing or backpack and is not removable.

Figure 6A:
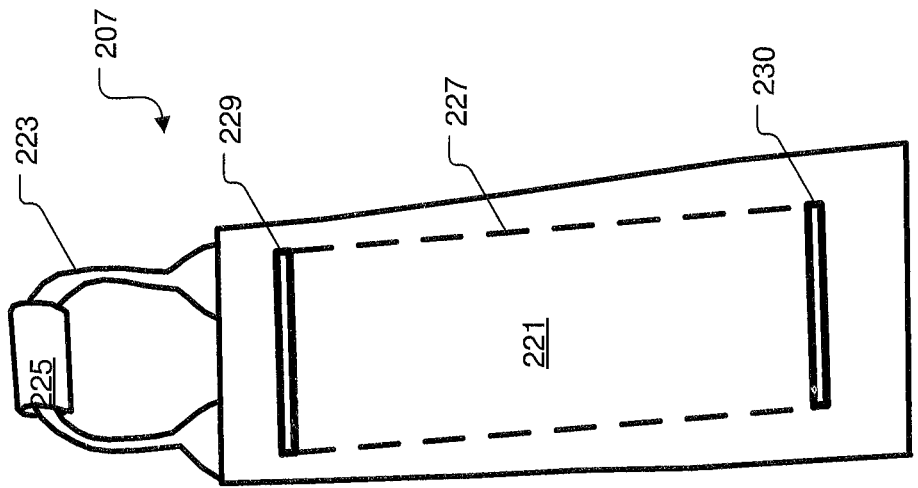
FIG. 6A is a generally downward perspective view of a tourniquet pouch with a cover removed according to the present application.
Figure 6B:
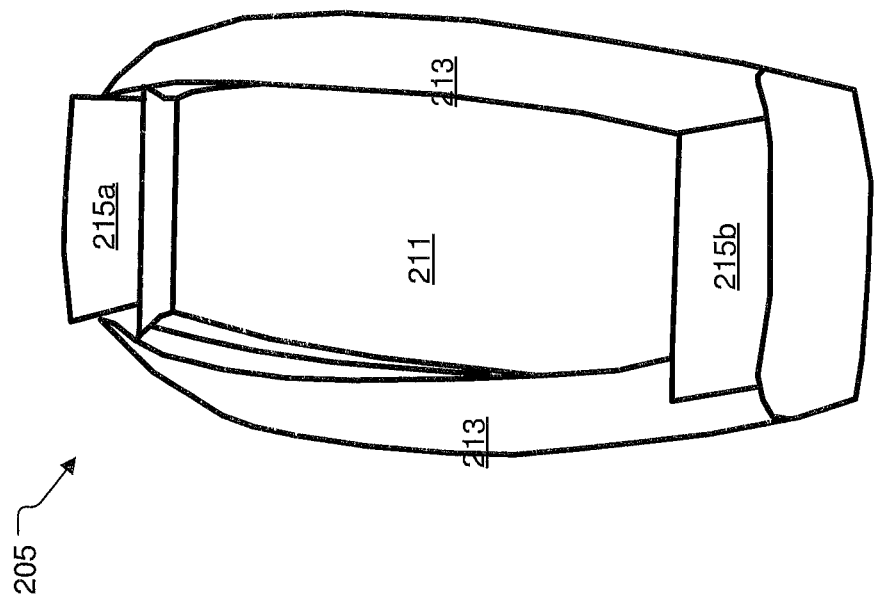
FIG. 6B is a generally downward perspective view of a tourniquet pouch cover removed from the pouch according to the present application.

FIG. 6A illustrates the pouch 205 with the cover 207 removed. Any contents stored inside of pouch 205 is readily available because the cover 207 is removed. Unlike conventional tourniquet holders, the pouch 205 does not require the user to yank the tourniquet out of a small opening.

It is apparent that a system with significant advantages has been described and illustrated. The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A holder for rapidly accessing a releasably retained tourniquet, comprising:
   a pouch having a rectangular shaped opening, the rectangular shaped opening spanning a first length of the pouch;
   wherein the pouch comprises:
      a lower member;
      a first side member attached to a first edge of the lower member;
      a second fixed side member attached to a second edge of the lower member;
   a fully-removable cover releasably attached around a perimeter of the rectangular shaped opening of the pouch, the cover spanning a second length, the second length greater than the first length;
   wherein the side members are fixed relative to at least one of the lower member and the fully-removable cover; and
   a slot enclosed within the cover;
      wherein the slot selectively retains a tail of the tourniquet prior to and upon removal of the cover;
   wherein the cover closes the rectangular shaped opening of the pouch; and
   wherein the cover is coupled to the pouch by hook and loop tape.

2. The holder according to claim 1, wherein the tourniquet is fully enclosed between the pouch and the cover.

3. The holder according to claim 1, further comprising:
   a mounting system.

4. The holder according to claim 3, further comprising:
   an opening between the mounting system and the pouch;
   wherein the opening is configured for retaining a belt.

5. The holder according to claim 3, the mounting system comprising:
   a plurality of straps;
   wherein the plurality of straps are configured for retaining a shoulder strap.

6. The holder according to claim 3, the mounting system comprising:
   a plurality of straps;
   wherein the plurality of straps are configured for retaining a malice clip.

7. The holder according to claim 1, further comprising:
   a handle located on a first end of the cover.

8. The holder according to claim 3, the mounting system comprising:
   a first adjustable strap;
   a second adjustable strap; and
   a plurality of fixed straps;
   wherein the plurality of fixed straps are located between the first adjustable strap and the second adjustable strap.

9. A tourniquet holder for rapidly accessing a tourniquet, comprising:
   a pouch having an elongated opening spanning a first length, the pouch comprising:
      a lower member;
      a first side member attached to a first edge of the lower member;
      a second side member attached to a second edge of the lower member;
      a first tab attached to a first end of the lower member; and
      a second tab attached to a second end of the lower member; and
   a fully-removable cover coupled to the pouch, the cover spanning a second length, the second length being greater than the first length;
   wherein the side members are fixed relative to at least one of the lower member and the fully-removable cover; and
   a slot enclosed within the cover;
      wherein the slot selectively retains a tail of the tourniquet prior to and upon removal of the cover;
   wherein the first side member, the second side member, the first tab, and the second tab all collectively form a rectangular shaped opening for storage of a tourniquet; and
   wherein the cover closes the rectangular shaped opening of the pouch; and
   wherein the cover is releasably attached to both the side members, the tail of the tourniquet, and at least one of the tabs of the pouch by hook and loop tape.

10. The holder according to claim 9, further comprising: a mounting system located on the lower member opposite the rectangular shaped opening.

11. The holder according to claim 10, the mounting system comprising:
    a first adjustable strap; and
    a second adjustable strap;
    wherein the first adjustable strap is adjacent the first end of the lower member; and
    wherein the second adjustable strap is adjacent the second end of the lower member.

12. The holder according to claim 11, the mounting system further comprising:
    a plurality of fixed straps;
    wherein the plurality of fixed straps are located between the first adjustable strap and the second adjustable strap.

13. The holder according to claim 9, further comprising: a handle located on a first end of the cover.

14. A tourniquet holder for rapidly releasing a tourniquet, comprising;
    a pouch having a rectangular shaped opening of a first length, the pouch comprising:
       a lower member;
       a first side member attached to a first edge of the lower member;
       a second side member attached to a second edge of the lower member;
       a first tab attached to a first end of the lower member;
       a second tab attached to a second end of the lower member;
    a fully-removable cover of a second length coupled to the pouch, the second length being greater than the first length;
       wherein the side members are fixed relative to at least one of the lower member and the fully-removable cover; and
    a slot enclosed within the fully-removable cover;
       wherein the slot selectively retains a tail of the tourniquet prior to and upon removal of the fully-removable cover;
    wherein the first side member, the second side member, the first tab, and the second tab all collectively form a rectangular shaped opening for storage of a releasably retained tourniquet;
    wherein the removable cover closes the rectangular shaped opening of the pouch; and
    wherein the removable cover is releasably attached around a perimeter of the rectangular shaped opening of the pouch by magnets.

15. The holder according to claim 14, further comprising:
    a mounting system located on the lower member opposite the rectangular shaped opening.

16. The holder according to claim 15, wherein the mounting system comprises:
    a first adjustable strap; and
    a second adjustable strap;
    wherein the first adjustable strap is adjacent the first end of the lower member; and
    wherein the second adjustable strap is adjacent the second end of the lower member.

17. The holder according to claim 16, wherein the mounting system further comprises:
    a plurality of fixed straps;
    wherein the plurality of fixed straps are located between the first adjustable strap and the second adjustable strap.

18. The holder according to claim 1, wherein the slot further comprises:
    a first opening; and
    a second opening;
    wherein the tail passes through the first opening and the second opening; and
    wherein the tourniquet remains releasably attached to the cover upon removal of the fully removable cover.

19. The holder according to claim 9, wherein the slot further comprises:
    a first opening; and
    a second opening;
    wherein the tail passes through the first opening and the second opening; and
    wherein the tourniquet remains releasably attached to the cover upon removal of the fully removable cover.

20. The holder according to claim 14, wherein both the first non-detachable side member and the second non-detachable side member are arc-shaped and elongated; and
    wherein the both the non-detachable side members are oriented perpendicular to the tabs.

* * * * *